(12) United States Patent
Fox

(10) Patent No.: US 8,268,335 B2
(45) Date of Patent: Sep. 18, 2012

(54) SKIN TREATMENT SYSTEMS

(75) Inventor: Charles Fox, Fair Lawn, NJ (US)

(73) Assignee: Greyson International, Inc., Coconut Creek, FL (US)

( * ) Notice: Subject to any disclaimer, the term of this patent is extended or adjusted under 35 U.S.C. 154(b) by 390 days.

(21) Appl. No.: 12/568,165

(22) Filed: Sep. 28, 2009

(65) Prior Publication Data

US 2010/0080764 A1 Apr. 1, 2010

Related U.S. Application Data

(63) Continuation-in-part of application No. 11/810,878, filed on Jun. 7, 2007, now abandoned, and a continuation-in-part of application No. PCT/US2008/066303, filed on Jun. 9, 2008.

(51) Int. Cl.
*A61K 8/02* (2006.01)
*A61K 51/00* (2006.01)
*A61M 36/14* (2006.01)
*C11D 1/62* (2006.01)

(52) U.S. Cl. .... 424/401; 424/1.69; 424/1.73; 424/70.28

(58) Field of Classification Search .................. None
See application file for complete search history.

(56) References Cited

U.S. PATENT DOCUMENTS

| | | | |
|---|---|---|---|
| 5,560,917 A | 10/1996 | Cohen et al. | |
| 5,616,332 A | 4/1997 | Herstein | |
| 5,989,536 A | 11/1999 | Deckner et al. | |
| 6,150,403 A | 11/2000 | Biedermann et al. | |
| 6,284,802 B1 | 9/2001 | Bissett et al. | |
| 6,387,382 B1 | 5/2002 | Saleh et al. | |
| 6,444,212 B1 * | 9/2002 | Cavazzuti et al. | 424/401 |
| 2004/0120918 A1 * | 6/2004 | Lintner et al. | 424/70.14 |
| 2005/0063932 A1 | 3/2005 | Dilallo et al. | |
| 2006/0198800 A1 * | 9/2006 | Dilallo et al. | 424/59 |
| 2008/0305057 A1 | 12/2008 | Fox | |

FOREIGN PATENT DOCUMENTS

WO 9503028 A1 2/1955

OTHER PUBLICATIONS

International Search Report and written opinion dated Dec. 29, 2008.

\* cited by examiner

*Primary Examiner* — Mina Haghighatian
*Assistant Examiner* — Mei-Ping Chui
(74) *Attorney, Agent, or Firm* — Laurence A. Greenberg; Werner H. Stemer; Ralph E. Locher

(57) ABSTRACT

A basic facial and body treatment cosmetic formulation is a combination of a cationic emulsifying agent, an oil soluble liquid polymer and a naturally occurring lactate buffer system. The basic formulation is a starter system that can be specialized to skin moisturizers, skin lighteners, skin pigmenting agents, sunscreens, antioxidants, line reducing products, wrinkle reducing products, anti-cellulite products, pharmaceuticals and the like.

4 Claims, No Drawings

SKIN TREATMENT SYSTEMS

This application is a Continuation-In-Part and claims benefit of U.S. patent application Ser. No. 11/810,878, filed Jun. 7, 2007 the disclosure of which is incorporated by reference in its entirety.

BACKGROUND OF THE INVENTION

1. Field of the Invention

The invention relates, generally, to facial and body treatment cosmetic and over-the-counter pharmaceutical formulations, which may include skin moisturizers; skin wrinkle and line reducers; sunscreens; eye creams; skin pigmentation preparations; anti-cellulite preparations; skin redness reduction creams; antioxidant preparations to fight free radicals; antiperspirants and deodorants; anti-itch preparations and the like.

2. Description of the Related Art

Most cosmetics and skin treatment pharmaceuticals on the market today utilize nonionic, anionic or a combination of these types of emulsifying agents to form stable oil-in-water emulsions. They are usually used at levels of from 4-6% by weight. Most facial and body treatment products contain about 75% water by weight. When these preparations are applied to the skin, the water evaporates and there is left on the skin about 12-24% by weight emulsifying agent at a pH range of from about 6-8. These residual emulsifying agents cause the remaining product to be water-soluble and active and useful ingredients in the product can be removed by perspiration from the user. But a more serious situation arises because the residual emulsifying agents can emulsify the important skin lipids that make up the protective barrier of the skin, and when the product is washed off the face or body in the evening these important protective lipids are also removed. This increases moisture loss and skin dryness and damages the lipid protective layer of the skin.

There is a clear need for cosmetic and pharmaceutical products that do not remove the important protective skin lipids thus leaving the skin with a better moisture level and at a more desirable pH.

SUMMARY OF THE INVENTION

It is accordingly an object of the invention to provide new and improved skin treatment systems, which overcome the herein-mentioned disadvantages of the heretofore-known formulations of this general type, which do not emulsify the skin lipids and maintains the skin at a more desirable pH level.

With the foregoing and other objects in view there is provided, in accordance with the invention, a base formulation. The base formulation includes a cationic emulsifying agent 1.50-5.00% wt; a liquid polymer 0.5-10.0% wt; a buffer with quantity sufficient for pH 3.8-6.2; and water remainder.

With the foregoing and other objects in view there is further provided, in accordance with the invention, a day cream with sunscreen. The day cream with sunscreen contains sunscreen 8.0-46.5% wt; a cationic emulsifying agent 1.00-5.00% wt; an oil soluble/dispersible liquid polymer 1.00-10.00% wt; moisturizing agents 8.6-14.45% wt; a buffer quantity sufficient to pH 3.8-6.2; and water remainder.

In accordance with an added feature of the invention, the sunscreen includes avobenzone 2.00-3.00% wt; octinoxate 5.00-7.50% wt; oxybenzone 3.00-6.00% wt; homosalate 5.00-15.00% wt; octisalate 2.00-5.00% wt; and octocrylene 3.00-10.00% wt.

In accordance with an additional feature of the invention, the oil soluble/dispersible liquid polymer includes PPG-12 SMDI copolymer 1.00-5.00% wt; and PPG-5 SMDI copolymer 0.10-0.75% wt.

In accordance with a further feature of the invention, the moisturizing agents include glyceryl stearate 1.45-3.00% wt; isocetyl stearate 0.75-3.00% wt; squalane 1.45-3.00% wt; sodium hyaluronate (1%) 1.35-5.00% wt; sodium PCA 1.25-3.00% wt; and saccharide isomerate 1.35-3.00% wt.

In accordance with another feature of the invention, a fatty alcohol of 1.00-3.00% wt is added.

In accordance with yet another feature of the invention, antioxidants of 1.65-5.00% wt are added. The antioxidants include superoxide dismutase 0.85-1.25% wt; green tea extract 0.75-3.00% wt; and vitamin C derivatives 0.05-3.00% wt.

In accordance with another further feature of the invention, phenoxyethanol 0.20-1.00% wt; methylparaben 0.10-0.75% wt; butylparaben 0.10-0.65% wt; propylparaben 0.05-0.55% wt; and iodopropynyl butyl carbamate 0.10-0.65% wt, are added.

A unique day cream with sunscreen formulation includes avobenzone 2.7-3.0% wt; octinoxate 5.0-7.50% wt; oxybenzone 3.00-6.00% wt; homosalate 5.00-15.00% wt; octisalate 2.00-5.00% wt; octocrylene 3.00-10.00% wt; PPG-12 SMDI copolymer 1.00-5.00% wt; PPG-51 SMDI copolymer 0.10-0.75% wt; steapyrium chloride 1.00-3.00% wt; glyceryl stearate 1.45-3.50% wt; cetyl alcohol 1.00-3.00% wt; isocetyl stearate 1.00-3.00% wt; squalane 1.00-5.00% wt; sodium hyaluronate (1%) 1.00-5.00% wt; sodium PCA 1.00-5.00% wt; saccharide isomerate 1.00-5.00% wt; superoxide dismutase 0.05-1.50% wt; green tea extract 0.75-3.00% wt; phenoxyethanol 0.20-1.00% wt; methylparaben 0.10-0.75% wt; butylparaben 0.10-0.65% wt; isopropylparaben 0.05-0.55% wt; iodopropynyl butyl carbamate 0.10-0.65% wt; lactate buffer qs to pH 3.8-6.2; and water remainder.

With the foregoing and other objects in view there is further provided, in accordance with the invention, a wrinkle cream. The wrinkle cream contains a cationic emulsifying agent 1.50-5.00% wt; an oil soluble liquid polymer 1.00-10.00% wt; anti-wrinkle agents 2.05-8.00% wt; a buffer quantity sufficient to pH 3.9-6.0; and water remainder.

In accordance with an added feature of the invention, the anti-wrinkle agents include palmitoyl pentapeptide-4 0.65-2.00% wt; palmitoyl tetraoeoptide-7 0.75-2.00% wt; ceramide 2 0.30-0.85% wt; and palmitoyl oligopeptide 0.35-1.00% wt.

In accordance with an additional feature of the invention, the oil soluble liquid polymer includes PPG-12 SMDI copolymer 1.00-5.00% wt; and PPG-51 SMDI copolymer 0.10-0.50% wt.

In accordance with another feature of the invention, moisturizing agents 4.10-7.64% wt; and antioxidants 0.20-1.25% wt, are added. Ideally, the moisturizing agents include glcyceryl stearate 1.00-3.00% wt; jojoba oil 0.65-3.00% wt; isocetyl stearate 0.65-3.000% wt; sodium hyaluronate 1.00-5.00% wt; and sodium PCA 0.75-3.00% wt. The antioxidants include vitamin A palmitate 0.05-0.50% wt; vitamin E acetate 0.10-3.00% wt; and vitamin C derivatives 0.05-2.00% wt.

In accordance with a further feature of the invention, a fatty alcohol 0.65-3.00% wt is added.

A preferred wrinkle cream formulation includes PPG-12 SMDI copolymer 2.25-3.15% wt; PPG-51 SMDI copolymer 0.10-0.50% wt; vitamin A palmitate 0.10-0.50% wt; vitamin E acetate 0.10-0.75% wt; vitamin C derivatives 0.05-2.00% wt; glcyceryl stearate 1.75-3.00% wt; distearyldimmonium chloride 1.70-5.00% wt; cetyl alcohol 0.75-3.00% wt; jojoba oil 0.65-3.00% wt; isocetyl stearate 0.65-3.00% wt; sodium hyaluronate 0.50-5.00% wt; sodium PCA 0.75-3.00% wt; palmitoyl pentapeptide-4 0.65-2.00% wt; palmitoyl tetraoeoptide-7 0.75-2.00% wt; ceramide 2 0.30-0.85% wt; palmitoyl oligopeptide 0.35-1.00% wt; lactate buffer qs to pH 3.9-6.00; and water remainder.

The above-described formulations moisturize the skin, last all day long, and make sure the skin is kept at the optimum pH so that it helps the skin repair itself.

Other characteristic features of the invention are set forth in the appended claims.

Although the invention is illustrated and described herein as embodied in new and improved skin treatment systems, it is nevertheless not intended to be limited to the details described, since various modifications and structural changes may be made therein without departing from the spirit of the invention and within the scope and range of equivalents of the claims.

The construction of the invention, however, together with additional objects and advantages thereof will be best understood from the following description of specific embodiments.

DESCRIPTION OF THE PREFERRED EMBODIMENTS

The inventive TRILEXON series of facial and body treatment cosmetic formulations is based on three principles.

First, the treatment cosmetic or pharmaceutical formulations use a polymer that is a blend of a liquid polymeric material compared to most other polymers used in cosmetics that are solid. This permits the polymer to spread easily and impart a soft, non-greasy, velvety feel to the skin. In addition to being a liquid, the polymer is insoluble in water and is thus not removable from the skin by sweating. But a further important property of the polymer is that it can dissolve the ingredients we use to treat the skin. In addition, the polymer releases the materials slowly over a 12-hour period and thus the skin receives treatment at a slow steady pace. Alternatively, the materials remain on the skin up to about 12 hours or until removed or washed off by the user.

Second, it has been scientifically proven that the enzymes present in the skin that synthesize the protective barrier of the skin, which holds moisture in the skin, are only active in a narrow pH range. The cosmetic and pharmaceutical formulations have a lactate buffer system that works in conjunction with the emulsifying system to keep the skin at this desired pH all day long.

Dermatologists have reported that the skin's protective barrier layer repairs itself only at a specific pH range. So the skin treatment products are formulated to maintain this pH range. To maintain the pH over 12 hours the treatment cosmetic and pharmaceutical formulations use a buffer. The buffer assures us that the pH will always remain at the correct level.

Third, the facial and body treatment cosmetics and pharmaceuticals use a positively charged emulsifying agent to uniformly combine all water and water insoluble components into a luxurious cream/lotion. This type of emulsifying agent is substantive to the skin, will not wash away and prolongs skin moisturization. Further, the emulsifying agent closely resembles the natural pH of the skin.

Preferably, the facial treatment cosmetic formulations use a cationic emulsifying agent. Cationic emulsifiers have a positive charge and attach themselves to the negatively charged skin after application to the skin. In essence, the emulsifying agent is lost and the product now becomes water insoluble and cannot be removed by perspiration of the user after application. In addition the cationic emulsifiers have a positive charge and the pH of the products formulated with them are on the acid side (e.g. pH 4 to 5). Cationic emulsifiers that may be used include steapyrium chloride, behetrimonium chloride, dicetyldimonium chloride, distearyldimonium chloride and the like. The preferred emulsifier is distearyldimonium chloride used at a level of 1.5-5% wt.

In addition a water insoluble polymer that has the ability to hold important skin treatment materials is used in the product. The polymer is preferably oil soluble, but non-oil soluble polymers may also be used as long as they are not water soluble, but can be emulsified in oil/water or water/oil emulsions. In an emulsion, the polymer is broken down into very small particles and holds within it critical oil and water soluble materials. After application to the skin the polymer then reforms into a water insoluble film and slowly releases during the day or evening the skin treatment materials included in the emulsion such as moisturizers, antioxidants, skin lightening agents, wrinkle and line reducing agents, skin pigmenting agents, skin lightening agents and the like. Such polymers include materials such as water insoluble carbomers, water insoluble cellulosics, water insoluble clays, water insoluble polyacrylates, and liquid polymers such as polyolprepolymer-2, polyolprepolymer-14, and polyolprepolymer-15 used in the range of 0.5-10% wt.

The buffer system in the facial treatment cosmetics is used to maintain the pH levels at 4.2-5.0. It has been shown that the enzymes present in the skin that initiate the production of the lipids required to form the protective skin barrier layer are activated only in this pH range. Products that leave the skin in a lower or higher pH range actually are doing harm to the skin by preventing these important enzymes from doing their work. Buffers used my include phosphate buffers, citrate buffers, lactate buffers and any other buffers listed in the chemical encyclopedias as long as they are water soluble and do not irritate the skin. Preferably, a lactate buffer system is used because lactic acid is a normal constituent of the skin.

The basic facial treatment cosmetic formulation is a combination of a cationic emulsifying agent, an oil soluble liquid polymer and a naturally occurring lactate buffer system. The basic formulation is a starter system that can be specialized to skin moisturizers, skin lighteners, skin pigmenting agents, sunscreens, antioxidants, line reducing products, wrinkle reducing products, anti-cellulite products, skin treatment pharmaceuticals and the like.

To make the product attractive to use, these skin treatment products have additional ingredients added. They include: low HLB moisturizing agents such as glyceryl stearate and propylene glycol stearate; fatty alcohols such as cetyl alcohol, stearyl alcohol, myristyl alcohol, behenyl alcohol and the like; moisturizing oils such as esters of high and low molecular weight alcohols esterified with fatty acids, such as isopropyl stearate, isocetyl stearate, jojoba wax; further moisturizing oils such as triglycerides such as avocado oil, sesame oil, and the like; moisturizing ingredients normally found in the skin such as sodium hyaluronate, sachharide isomerate, and pyrrolidone carboxylic acid salts. Antioxidants are included to protect the skin from free radicals which form when the skin is exposed to UVA and UVB rays, such as green tea extract, ginko nut extract, grape seed extract, superoxide dismutase and vitamins A, C and E.

For the treatment of lines and wrinkles we have added ceramide 2, PEG-10 rapeseed sterol, palmitoyl oligopeptide, and palmitoyl tetrapeptide-7.

Example 1

Day Cream with Sunscreen Formula

Active Ingredients

| | |
|---|---|
| avobenzone | 2.7-3.0% wt; |
| octinoxate | 7.0-7.50% wt; |
| oxybenzone | 5.5-6.00% wt; |

Inactive Base Ingredients

| | |
|---|---|
| PPG-12 SMDI copolymer | 2.25-3.15% wt; |
| PPG-51 SMDI copolymer | 0.10-0.75% wt; |
| steapyrium chloride | 1.00-3.00% wt; |
| glyceryl stearate | 1.45-3.00% wt; |
| cetyl alcohol | 1.00-2.50% wt; |
| isocetyl stearate | 1.00-3.00% wt; |
| squalane | 1.00-3.00% wt; |
| sodium hyaluronate (1%) | 1.00-5.00% wt; |
| sodium PCA | 1.00-5.00% wt; |
| saccharide isomerate | 1.00-5.00% wt; |
| superoxide dismutase | 0.05-1.50% wt; |
| green tea extract | 0.50-3.00% wt; |
| phenoxyethanol | 0.20-1.00% wt; |
| methylparaben | 0.10-0.75% wt; |
| butylparaben | 0.10-0.65% wt; |
| propylparaben | 0.05-0.55% wt; |
| iodopropynyl butyl carbamate | 0.10-0.65% wt; |
| lactate buffer qs to pH | 3.8-6.2 |
| water | qs to 100.00 (remainder). |

Example 2

Wrinkle and Line Reducing Cream Formula

| | |
|---|---|
| PPG-12 SMDI copolymer | 1.00-5.00% wt; |
| PPG-51 SMDI copolymer | 0.10-0.50% wt; |
| vitamin A palmitate | 0.05-0.50% wt; |
| vitamin E acetate | 0.10-0.75% wt; |
| glcyeryl stearate | 1.50-3.00% wt; |
| distearyldimmonium chloride | 1.50-5.00% wt; |
| cetyl alcohol | 0.75-2.00% wt; |
| jojoba oil | 0.65-2.00% wt; |
| isocetyl stearate | 0.65-3.00% wt; |
| sodium hyaluronate | 0.50-2.00% wt; |
| sodium PCA | 0.75-3.00% wt; |
| palmitoyl pentapeptide-4 | 0.65-2.00% wt; |
| palmitoyl tetraoeptide-7 | 0.75-2.00% wt; |
| ceramide 2 | 0.30-0.85% wt; |
| palmitoyl oligopeptide | 0.35-0.75% wt; |
| lactate buffer | qs to pH 3.9-6.00 |
| water (quantity sufficient) | qs to 100.00 (remainder). |

Example 3

Preparation in Two Phases

Phase 1

| | |
|---|---|
| Distearyldimonium Chloride | 1.50-5.00% w/w |
| Saccharide Isomerate | 1.00-5.00% w/w |
| Glycerin | 1.00-5.00% w/w |
| Butylene Glycol | 1.00-5.00% w/w |
| Sodium Lactate | 0.5-2.00% w/w* |
| Lactic Acid | 0.01-0.50% w/w* |
| PPG-51/SMDI Copoiymer | 0.10-2.00% w/w |
| Water | 50-65% w/w |

Phase 2

| | |
|---|---|
| Glyceryl Stearate | 1.00-5.00% w/w |
| Propylene Glycol Stearate | 0.50-5.00% w/w |
| Cetyl Alcohol | 0.50-3.00% w/w |
| Jojoba Oil Refined | 0.50-3.00% w/w |
| Isocetyl Stearate | 0.50-5.00% w/w |
| Dow Corning Fluid 345 | 0.50-3.00% w/w |
| Euxyl PE 9010 | 1.00-2.00% w/w |
| C12-15 Alkyl Benzoate | 1.00-5.00% w/w |
| Ceramides | 0.10-1.00% w/w |
| Soy Sterols | 0.50-2.00% w/w |
| PPG-12/SMDI Copolymer | 0.50-10.00% w/w |

Percentages are total weight of the final composition.

Polyolprepolymer 15 is a water soluble copolymer; CAS #39444-87-6; INCI Name assigned to this material is PEG-8/SMDI Copolymer.

Polyolprepolymer 2 is a water insoluble copolymer; CAS #9042-82-4; INCI Name assigned to this material is PPG-12/SMDI Copolymer.

Polyolprepolymer 14 is a water insoluble copolymer; CAS #9042-82-4; INCI Name assigned to this material is PPG-51/SMDI Copolymer.

The composition is prepared as follows:

The components of Phase 1 are placed in a suitable steam jacketed stainless kettle and heated to 70-75° C. They are mixed intermittently until an opaque, homogeneous, low viscosity gel has formed. Temperature of the composition is maintained at 70-75° C.

The components of Phase 2 are placed in a suitable steam jacketed stainless kettle and heated to 75-85° C. with intermittent stirring until clear and homogeneous. The mixture of phase 2 is cooled to 70-75° C. Once the mixture of Phase 2 has reached the desired temperature range, the mixture of Phase 2 is added to the mixture of Phase 1 using a homomixer, homogenizer, or equivalent. Use of a propeller or gate mixer should be avoided because proper combination requires that the formation of a vortex and air incorporation be avoided and minimized.

Continue homogenization and allow the combined phase to cool while homogenizing. When the resultant emulsion has cooled to approximately 25-30° C., quality control testing is performed to ensure compliance with desired finished product specifications.

In one embodiment, the finished product is tested according to the following specifications:

| | |
|---|---|
| Appearance: | Soft ivory colored, unperfumed cream or lotion |
| Water content: | 50-65% |
| pH: | 4.50-5.00 (Note: sodium lactate solution or lactic acid solution may be used to adjust the pH if necessary) |
| Fragrance: | unperfumed |
| Preservatives: | no parabens for safety |

In one embodiment, the composition is formed as follows

Phase 1

| | |
|---|---|
| Distearyldimonium Chloride | 4.50 grams |
| Saccharide Isomerate | 1.45 gram |
| Glycerin | 5.00 grams |
| Butylene Glycol | 1.00 gram |
| Sodium Lactate | 2.00 grams |
| Lactic Acid | 0.05 grams |
| PPG-51/SMDI Copolymer | 0.50 grams |
| Water | 65.00 grams |

Phase 2

| | |
|---|---|
| Glyceryl Stearate | 2.00 grams |
| Propylene Glycol Stearate | 0.50 grams |
| Cetyl Alcohol | 2.00 grams |
| Jojoba Oil Refined | 3.00 grams |
| Isocetyl Stearate | 2.00 grams |
| Dow Corning Fluid 345 | 1.00 gram |
| Euxyl PE 9010 | 1.00 gram |
| C12-15 Alkyl Benzoate | 3.00 grams |
| Ceramides | 0.50 grams |
| Soy Sterols | 0.50 grams |
| PPG-12/SMDI Copolymer | 5.00 grams |

This is a base composition for a unique cosmetic delivery system. Products prepared for skin moisturization, skin anti-aging, dark circles under the eyes, lines and wrinkles, skin tightening. pore reduction, etc will require the addition of additional appropriate active ingredients to meet claims made, but the basic, structure of the delivery system will remain fixed according to the formulation of Example 3.

Most cosmetic and proprietary drug emulsions utilize mainly anionic and/or nonionic emulsifying agents. The anionic and/or nonionic emulsifying agents are not destroyed after application to the skin but they emulsify the protective naturally occurring skin emollients that form the barrier layer and when the user washes off the preparation at bed time they wash off all of the important skin and barrier layer emollients and leave the skin in a worse and drier condition. The formulation of Example 3 uses only a cationic emulsifier. When the preparation is applied to the skin, the positively charged cationic emulsifying agent combines with the negatively charged skin and its emulsifying power is destroyed. Accordingly no matter how long the preparation is allowed to remain on the skin it will not emulsify or remove the skin's natural and protective emollients when the preparation is washed off at night. Enzymes that repair the skin's natural protective barrier are only active in the pH range of 4.5-5.5. The skin's lipid barrier recovery is impeded at neutral pH values. The enzyme responsible is Beta-glucoocerebrosidase. Its activity at pH 4.5-5.5.

Most cosmetics and proprietary drugs are above this active pH range and cannot repair a damaged skin barrier. The preferred buffer system is a lactate buffer to pH 4.5-5.5. Lactates are present in the human skin and are excellent skin moisturizers. Naturally occurring enzymes that can heal damaged skin only are active in this pH range. A damaged skin barrier will lead to excessive moisture loss and a dry skin condition.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A base formulation, which comprises:
    (a) a first phase comprising:
    a single emulsifier of distearyldimonium chloride 1.50-5.00% w/w;
    saccharide isomerate 1.00-5.00% w/w;
    glycerin 1.00-5.00% w/w;
    butylene glycol 1.00-5.00% w/w;
    sodium lactate 0.5-2.00% w/w;
    lactic acid 0.01-0.50% w/w;
    PPG-51/SMDI copolymer 0.10-2.00% w/w;
    water 50-65% w/w;
    wherein said sodium lactate and said lactic acid form a lactate buffer having a pH range of 3.8-6.2;
    (b) a second phase comprising:
    glyceryl stearate 1.00-5.00% w/w;
    propylene glycol stearate 0.50-5.00% w/w;
    cetyl alcohol 0.50-3.00% w/w;
    jojoba oil refined 0.50-3.00% w/w;
    isocetyl stearate 0.50-5.00% w/w;
    decamethylcyclopentasiloxane/dodecamethyl cyclohexasiloxane 0.50-3.00% w/w;
    2-phenoxyethanol/3-[(2-ethylhexyl)oxy]-1,2-propandiol 1.00-2.00% w/w;
    $C_{12-15}$ alkyl benzoate 1.00-5.00% w/w;
    ceramides 0.10-1.00% w/w;
    soy sterols 0.50-2.00% w/w;
    PPG-12/SMDI copolymer 0.50-10.00% w/w; and
    said second phase is combined with said first phase to form a cream base that releases an active ingredient over a period of time up to or about 12 hours;
    wherein each of said first and second phase weights are based on the weight of the base formulation when phases are combined; wherein the single emulsifier is present as the sole emulsifier in the base formulation.

2. A base according to claim 1 further comprises anti-wrinkle agents 2.05-8.00% wt; based on the total weight of the final formulation.

3. The base of claim 2, wherein said anti-wrinkle agents include: palmitoyl pentapeptide-4 0.65-2.00% wt; palmitoyl tetrapeptide-7 0.75-2.00% wt; ceramide-2 0.30-0.85% wt; and palmitoyl oligopeptide 0.35-1.00% wt, based on the total weight of the final formulation.

4. The base of claim 2, wherein said anti-wrinkle agents are selected from the group consisting of ceramide 2, PEG-10 rapeseed sterol, palmitoyl oligopeptide, and palmitoyl tetrapeptide-7.

* * * * *